US009606035B2

(12) United States Patent
Williams et al.

(10) Patent No.: US 9,606,035 B2
(45) Date of Patent: Mar. 28, 2017

(54) SYSTEM FOR MECHANICAL STIMULATION AND CHARACTERIZATION OF BIOLOGIC SAMPLES

(75) Inventors: Chrysanthi Williams, Minnetonka, MN (US); Troy D. Nickel, Minneapolis, MN (US); Brock N. Jacobites, Westborough, MA (US); Harry Malkasian, Westford, MA (US); Aaron M. Owens, Plymouth, MN (US)

(73) Assignee: TA Instruments-Waters LLC, Milford, MA (US)

( * ) Notice: Subject to any disclaimer, the term of this patent is extended or adjusted under 35 U.S.C. 154(b) by 890 days.

(21) Appl. No.: 13/332,495

(22) Filed: Dec. 21, 2011

(65) Prior Publication Data

US 2013/0160577 A1 Jun. 27, 2013

(51) Int. Cl.
| | |
|---|---|
| C12M 1/36 | (2006.01) |
| C12M 1/38 | (2006.01) |
| C12M 3/00 | (2006.01) |
| C12M 1/00 | (2006.01) |
| G01N 3/02 | (2006.01) |
| G01N 3/32 | (2006.01) |
| C12M 1/42 | (2006.01) |

(52) U.S. Cl.
CPC ............. *G01N 3/32* (2013.01); *C12M 35/04* (2013.01); *G01N 2203/0089* (2013.01); *G01N 2203/0242* (2013.01); *G01N 2203/0274* (2013.01)

(58) Field of Classification Search
CPC ........... C12M 35/04; G01N 2203/0089; G01N 2203/0242; G01N 2203/0274; G01N 3/32
USPC ................. 435/286.1, 289.1; 73/856, 856.3
See application file for complete search history.

(56) References Cited

U.S. PATENT DOCUMENTS

| | | |
|---|---|---|
| 4,833,083 A | 5/1989 | Saxena |
| 5,216,723 A | 6/1993 | Froeschle et al. |
| 5,306,305 A | 4/1994 | Lee |
| 5,735,896 A | 4/1998 | Amon et al. |
| 5,763,267 A | 6/1998 | Kurjan et al. |
| 5,792,603 A | 8/1998 | Dunkelman et al. |

(Continued)

FOREIGN PATENT DOCUMENTS

| | | |
|---|---|---|
| EP | 2130904 A2 | 12/2009 |
| WO | WO 2011143294 A2 * | 11/2011 |

OTHER PUBLICATIONS

International Search Report and Written Opinion dated Mar. 27, 2013 for International Application No. PCT/US2012/065756.

(Continued)

*Primary Examiner* — Nathan Bowers
*Assistant Examiner* — Lydia Edwards
(74) *Attorney, Agent, or Firm* — McCarter & English, LLP; Deborah M. Vernon (57) ABSTRACT

A system for applying mechanical stimulation to a biologic sample includes a first biologic sample chamber having a biologic sample holder therein, a support structure for holding the first biologic sample chamber, and a first actuator that can supply a mechanical load to a biologic sample held by the biologic sample holder. The actuator is configured to move into a first position proximate to the chamber in which the actuator can transmit the load to the biologic sample via a first transmission path that includes the biologic sample holder. A controller is configured to automatically move the first actuator into the first position.

37 Claims, 9 Drawing Sheets

(56) References Cited

U.S. PATENT DOCUMENTS

| | | | |
|---|---|---|---|
| 5,827,729 A | 10/1998 | Naughton et al. |
| 5,843,766 A | 12/1998 | Applegate et al. |
| 5,846,828 A | 12/1998 | Peterson et al. |
| 5,849,206 A | 12/1998 | Amon et al. |
| 5,928,845 A | 7/1999 | Feumi-Jantou |
| 5,976,826 A | 11/1999 | Singhvi et al. |
| 6,008,049 A | 12/1999 | Naughton et al. |
| 6,066,495 A | 5/2000 | Fofonoff et al. |
| 6,074,871 A | 6/2000 | Koontz |
| 6,080,581 A | 6/2000 | Anderson et al. |
| 6,121,042 A | 9/2000 | Peterson et al. |
| 6,207,405 B1 | 3/2001 | Bakich et al. |
| 6,210,957 B1 | 4/2001 | Carpentier et al. |
| 6,218,182 B1 | 4/2001 | Naughton et al. |
| 6,245,555 B1 | 6/2001 | Curtis |
| 6,281,007 B1 | 8/2001 | Fofonoff et al. |
| 6,368,838 B1 | 4/2002 | Singhvi et al. |
| 6,405,559 B1 | 6/2002 | Yoneda |
| 6,416,995 B1 | 7/2002 | Wolfinbarger |
| 6,503,273 B1 | 1/2003 | McAllister et al. |
| 6,589,525 B2 | 7/2003 | Gault |
| 6,592,623 B1 | 7/2003 | Bowlin et al. |
| 6,632,651 B1 | 10/2003 | Nevo et al. |
| 6,632,658 B1 | 10/2003 | Schoeb |
| 6,670,169 B1 | 12/2003 | Schob et al. |
| 6,864,084 B2 | 3/2005 | Schob |
| 6,943,008 B1 | 9/2005 | Ma |
| 6,962,814 B2 | 11/2005 | Mitchell et al. |
| 6,979,308 B1 | 12/2005 | MacDonald et al. |
| 6,991,628 B2 | 1/2006 | Vito et al. |
| 6,994,883 B2 | 2/2006 | Layrolle et al. |
| 7,029,838 B2 | 4/2006 | Williams et al. |
| 7,052,829 B2 | 5/2006 | Williams et al. |
| 7,067,306 B2 | 6/2006 | Singhvi et al. |
| 7,112,218 B2 | 9/2006 | McAllister et al. |
| 7,122,371 B1 | 10/2006 | Ma |
| 7,410,792 B2 | 8/2008 | Vilendrer |
| 7,587,949 B2 | 9/2009 | Dingmann et al. |
| 7,694,593 B2 | 4/2010 | Owens et al. |
| 2002/0022137 A1 | 2/2002 | Breme |
| 2002/0055166 A1 | 5/2002 | Cannon et al. |
| 2002/0090725 A1 | 7/2002 | Simpson et al. |
| 2002/0106625 A1 | 8/2002 | Hung et al. |
| 2002/0116054 A1 | 8/2002 | Lundell et al. |
| 2002/0146817 A1 | 10/2002 | Cannon et al. |
| 2003/0199083 A1 | 10/2003 | Vilendrer et al. |
| 2004/0009600 A1 | 1/2004 | Bowlin et al. |
| 2004/0037813 A1 | 2/2004 | Simpson et al. |
| 2004/0058434 A1 | 3/2004 | Gault |
| 2004/0147015 A1 | 7/2004 | El-Haj et al. |
| 2004/0203147 A1 | 10/2004 | Triffitt et al. |
| 2004/0219659 A1 | 11/2004 | Altman et al. |
| 2004/0241835 A1 | 12/2004 | Hutmacher et al. |
| 2004/0248722 A1 | 12/2004 | Mason et al. |
| 2005/0002910 A1 | 1/2005 | Wolfinbarger et al. |
| 2005/0009179 A1 | 1/2005 | Gemmiti et al. |
| 2005/0084951 A1 | 4/2005 | Rouhani et al. |
| 2005/0095711 A1 | 5/2005 | More |
| 2005/0102025 A1 | 5/2005 | Laroche et al. |
| 2005/0153436 A1* | 7/2005 | Vilendrer .................. 435/289.1 |
| 2006/0019388 A1 | 1/2006 | Hutmacher et al. |
| 2006/0024822 A1 | 2/2006 | Chang et al. |
| 2006/0141623 A1 | 6/2006 | Smith et al. |
| 2006/0223047 A1 | 10/2006 | Dancu et al. |
| 2006/0223175 A1 | 10/2006 | Hu et al. |
| 2006/0239981 A1 | 10/2006 | Yoo et al. |
| 2006/0270028 A1 | 11/2006 | More |
| 2007/0169572 A1* | 7/2007 | Schulz et al. ................ 73/865.3 |
| 2009/0019950 A1 | 1/2009 | Dingmann et al. |
| 2009/0282927 A1 | 11/2009 | Owens et al. |
| 2009/0326889 A1 | 12/2009 | Dingmann et al. |
| 2010/0313683 A1 | 12/2010 | Nickel et al. |

OTHER PUBLICATIONS

Davies, et al; Mechanically Loaded Ex Vivo Bone Culture System 'Zetos, Systems and Culture Preparation, CEMur oDpaevaine sC eetl las la. nd Materials vol. 11. 2006 (pp. 5 7-7 5 ).

Bose Corporation—ElectroForce Systems Group, BioDynamic® Test Instrument Product Guide and Specifications Brochure.

Bose Corporation—ElectroForce Systems Group, Multi-specimen BioDynamic® Test Instruments, Multi-specimenBioDynamic® Test Instrument Specifications 022009 Brochure.

Bose Corporation—ElectroForce Systems Group, ElectroForce® 5900 BioDynamic® Test Instrument, ElectroForce® 5900 BioDynamic Test Instrument Product Guide and Specifications Brochure.

* cited by examiner

SYSTEM FOR MECHANICAL STIMULATION AND CHARACTERIZATION OF BIOLOGIC SAMPLES

BACKGROUND

This disclosure relates to a system for applying a load to one or more biologic samples. "Biologic samples" may be living or dead tissue or biomaterials, such as biological, synthetic or manufactured biomaterials, medical devices, biosensors or combinations thereof. U.S. Pat. No. 7,694,593 (the '593 patent) discloses a multi-biologic sample conditioning system in which an actuator drives a push-bar assembly 120. The push-bar assembly 120 couples an axial displacement of the push-bar assembly to a biologic sample grip inside each biologic sample chamber 105. The lower biologic sample grip 250 mechanically transmits a user-defined conditioning profile generated by the actuator to a biologic sample held in the grips 250, 255.

When biologic samples including a biologic material are conditioned, they may be conditioned for a period of time (e.g. 10 minutes) followed by a rest period of time (e.g. 50 minutes). During this rest time the actuator shown in the '593 patent is not being utilized resulting in inefficiency in the system. In addition, only a single actuator is used in the system disclosed in the '593 patent and all biologic samples must undergo exactly the same loading timing regardless of differences in properties. As such, the type and timing of conditioning that the biologic samples can receive are limited by the particular type and timing of the actuator used in the system.

SUMMARY

In one aspect, a system for applying mechanical stimulation to a biologic sample includes a first biologic sample chamber having a biologic sample holder therein, a support structure for holding the first biologic sample chamber, and a first actuator that can supply a mechanical load to a biologic sample held by the biologic sample holder. The actuator is configured to move into a first position proximate to the chamber in which the actuator can transmit the load to the biologic sample via a first transmission path that includes the biologic sample holder. A controller is configured to automatically move the first actuator into the first position.

Embodiments may include one or more of the following features. The actuator can be automatically moved to a second position in which the actuator cannot transmit the load to the biologic sample. The actuator can be automatically moved to a third position proximate to a second biologic sample chamber having a second biologic sample holder therein so that the actuator can transmit a load to a biologic sample held by the second biologic sample holder via a transmission path that includes the second biologic sample holder. The system can further include a second actuator which is substantially different from the first actuator, the second actuator being automatically movable into the first position when the first actuator is not in the first position so that the second actuator can transmit a load to the first biologic sample holder via the first transmission path. The second actuator can be automatically moved to (i) a second position in which the second actuator cannot transmit a load to the first biologic sample, and (ii) a third position proximate to a second biologic sample chamber having a second biologic sample holder therein so that the second actuator can transmit a load to a biologic sample held by the second biologic sample holder via a transmission path that includes the second biologic sample holder when the first actuator is not in the third position.

Embodiments may include one or more of the following features. Each biologic sample chamber includes a first opening through which a fluid can be supplied to a biologic sample in that chamber, and wherein a first end of respective supply conduits is connected to each opening for conducting fluid to that opening. A second end of each respective conduit is connected to a first common conduit structure. Each biologic sample chamber includes a second opening through which a fluid can be transferred from that chamber. A first end of respective exhaust conduits is connected to each second opening for conducting fluid from the second opening. A second end of each respective conduit is connected to a second common conduit structure. The biologic sample is a living tissue sample. The actuator is an electromagnetic actuator. The controller causes the actuator to deliver the load. The controller is programmable by a user. The controller is configured to deliver the load for a user-defined period of time. The controller is configured to deliver the load according to a user-defined conditioning profile. The user-defined conditioning profile delivers the load to the biologic sample based upon one or more fixed-time profiles. The user-defined conditioning profile delivers the load to the biologic sample based upon a value of a measured variable. The measured variable consists of one or more of the following: temperature in the chamber, pH in the chamber, and a property of the biologic sample. After the actuator is moved away from the first position, a load on the biologic sample can be automatically maintained. The system further includes a fluid pump that can be operated to transmit pressure through a fluid in the chamber to thereby stimulate the biologic sample.

In another aspect, a system for applying mechanical stimulation to a biologic sample includes a first biologic sample chamber having a biologic sample holder therein and a support structure for holding the first biologic sample chamber. A first actuator can supply a first load to a biologic sample held by the biologic sample holder. The actuator is automatically movable into a first position proximate to the chamber in which the actuator can transmit the first load to the biologic sample via a first transmission path that includes the biologic sample holder. A second actuator can supply a second load to the biologic sample. The second actuator is automatically movable into the first position when the first actuator is not in the first position so that the second actuator can transmit the second load to the biologic sample via the first transmission path.

Embodiments may include one or more of the following features. The second actuator is substantially different from the first actuator. The first actuator can be automatically moved to a second position in which the actuator cannot transmit a load to the biologic sample. The system includes a second biologic sample chamber having a biologic sample holder therein. The support structure is capable of removably holding the second biologic sample chamber. The first actuator is automatically movable into a third position in which the first actuator is proximate to the second chamber so that the first actuator can transmit the first load to a biologic sample in the second chamber via a second transmission path that includes the second chamber's biologic sample holder. The second actuator can be automatically moved into the third position when the first actuator is not in the third position so that the second actuator can transmit the second load to a biologic sample in the second chamber via the second transmission path. Each biologic sample chamber includes an opening through which a fluid can be supplied to a biologic sample in that chamber. A first end of respective conduits is connected to each opening for conducting fluid to that opening. A second end of each respective conduit is connected to a common conduit structure. Each biologic sample chamber includes an opening through which a fluid can be transferred from that chamber. The biologic sample is a living tissue sample. The first and second actuators are each an electromagnetic actuator. After the first actuator is moved away from the first position, a load on the biologic sample can be automatically maintained.

In yet another aspect, a method for applying mechanical stimulation to a biologic sample includes providing a first biologic sample chamber having a biologic sample holder therein for holding a biologic sample. The chamber has a first opening through which a fluid can be supplied to the biologic sample and a second opening through which a fluid can be transferred from the chamber. The first and second openings have connected thereto a first end of respective conduits extending therefrom for conducting fluid. The chamber is attached to a support structure which can removably hold the biologic sample chamber. A first actuator that can supply a load to the biologic sample is automatically moved into a first position in which the actuator is proximate to the chamber whereby the actuator can transmit a load to the biologic sample by a first transmission path that includes the biologic sample holder.

Embodiments may include one or more of the following features. The actuator is automatically moved to a second position in which the actuator cannot transmit a load to the biologic sample. The actuator is automatically moved to a third position in which the actuator is proximate to a second chamber such that the actuator can transmit a load to a biologic sample in the second chamber via a second transmission path that includes a biologic sample holder in the second chamber. A second actuator which is substantially different from the first actuator is provided. The second actuator is automatically movable into (i) the first position when the first actuator is not in the first position so that the second actuator can transmit a load to the biologic sample in the first chamber via the first transmission path, and (ii) the third position when the first actuator is not in the third position so that the second actuator can transmit a load to a biologic sample in the second chamber via a second transmission path that includes a biologic sample holder in the second chamber. After the first actuator is moved to the second position, a load on the biologic sample can be automatically maintained. The actuator includes a driveshaft. A shaft extends from the biologic sample holder such that a free end of the shaft is external to the chamber. The shaft forms part of the first transmission path. Moving the actuator into the first position causes the driveshaft to be engaged with the shaft such that the driveshaft and shaft can be temporarily locked together.

In still a further aspect, a system for applying mechanical stimulation to a biologic sample includes a first biologic sample chamber having a biologic sample holder therein and a support structure for holding the first biologic sample chamber. A first actuator can supply a mechanical load to a biologic sample held by the biologic sample holder. The actuator is configured to move into a first position proximate to the chamber in which the actuator can transmit the load to the biologic sample via a first transmission path that includes the biologic sample holder. A measurement device obtains one or more characteristics of the biologic sample.

A controller is configured to automatically move the first actuator into the first position.

Embodiments may include one or more of the following features. The measurement device moves with the first actuator. The measurement device remains with the chamber even when the first actuator is moved away from the chamber.

DETAILED DESCRIPTION

Biologic research and development may require the growth and/or testing of a large number of biologic samples over time. Such biologic research and development often involve mechanical stimulation of the individual biologic samples. And such mechanical stimulation is often not continuous nor the same for all biologic samples. For example, a researcher may choose to stimulate and/or characterize one biologic sample at a first force and frequency for a first time period (e.g., a fixed time period or until some biologic sample condition is achieved) and stimulate and/or characterize a second biologic sample at a different force and frequency for a different time period (e.g., a different fixed time period or until some other biologic sample condition is achieved).

Electromagnetic actuators provide clean, precise, and repeatable mechanical stimulation to such biologic samples, but such actuators are often an expensive component to a biologic system. Some systems, such as the Multi-Chamber ElectraForce® BioDynamic® test instrument from Bose Corporation, provide multi-specimen mechanical stimulation using a shared motor. This type of system, however, cannot easily be scaled to a larger scale system capable of stimulating and characterizing a significantly greater number of biologic samples. Moreover, such a system lacks the ability to individually stimulate the specimens (at least with respect to mechanical stimulation). A system that provides the ability to use a number of motors that is less than the number of samples to individually stimulate multiple biologic samples allows a researcher to "time-shift" individual biologic sample stimulation periods so that the motor(s) (an expensive system component) may be better utilized than a motor on a system having individual motors for each biologic sample. Such a system allows for the customization of the mechanical stimulation profile since a motor(s) is dedicated to a biologic sample but only for a prescribed period of time. Such a system also provides a researcher more flexibility in specifying mechanical stimulation periods for individual biologic samples than systems that use a single motor (or set of motors) to stimulate multiple biologic samples simultaneously (such as the Multi-Chamber ElectraForce® BioDynamic® test instrument mentioned above).

Figure 8:
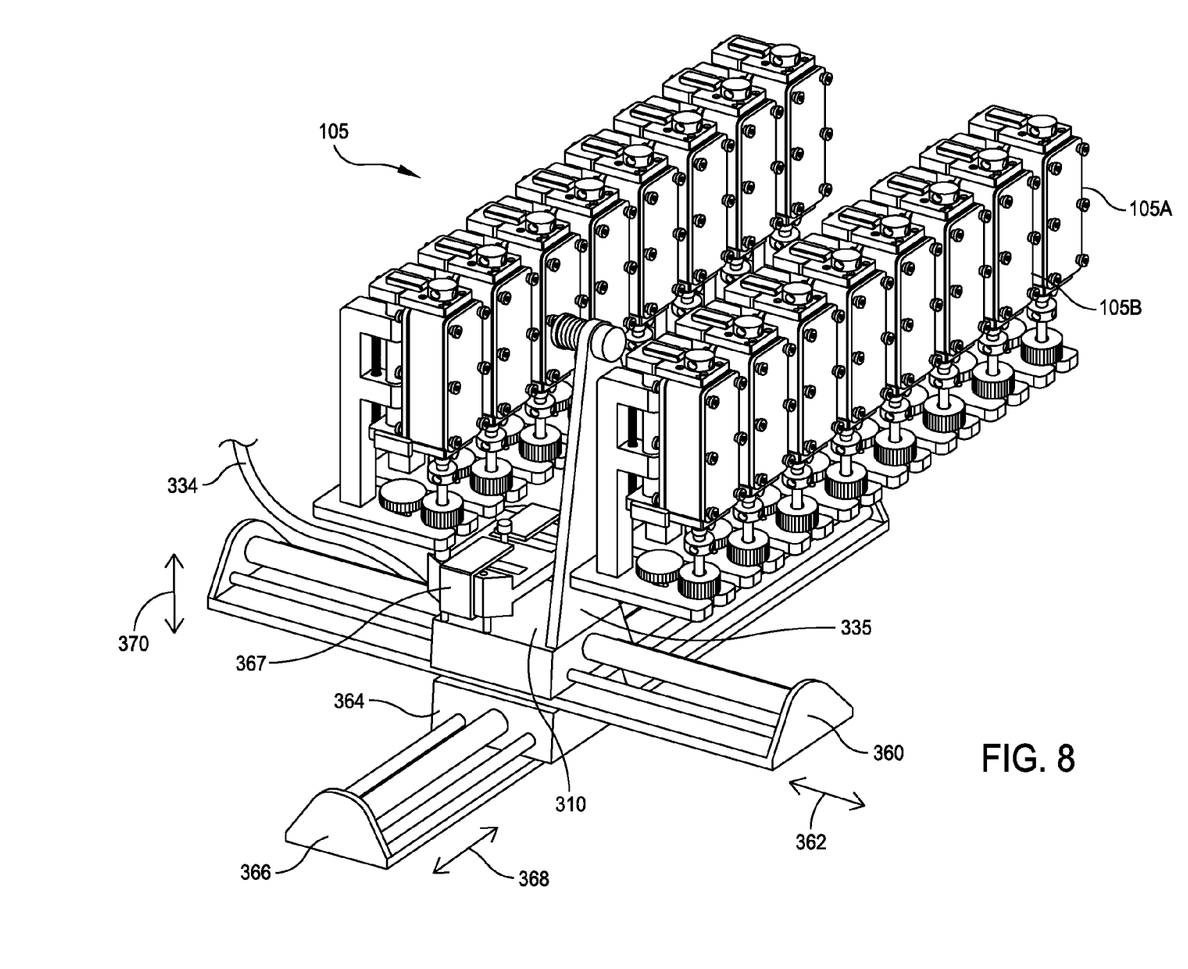
FIG. 8 is a perspective view of a system for applying mechanical stimulation to a plurality of biologic samples that are each contained in a biologic sample chamber.

FIG. 8 (described in further detail later in the application) shows an example of a biologic testing system that provides increased motor utilization while providing flexibility in mechanical stimulation profiles of biologic samples. In this example, a single motor system 367 is moved by a controller between sixteen biologic sample chambers (e.g. 105A and 105B). The controller preferably includes a user interface that permits a researcher (or other user) to specify various parameters of the mechanical stimulation to create a stimulation profile for each biologic sample. Depending on the system capabilities, the stimulation parameters may include the duration of stimulation (e.g., fixed time period or variable based on achievement of a measured condition), the type of stimulation (tension, compression, torsion, bend, radial, shear, fluid flow, pressure, electrical, magnetic etc), the frequency and magnitude of stimulation, and any other relevant stimulation parameters. And the simulation profile for each biologic sample may be identical or different in one or more parameters.

Moving one or a small number of actuators to the chamber(s) is preferred over moving the chamber(s) to the actuator(s), particularly where a large number of chambers or a various or changing combination of actuator types is involved. This is because each chamber will often have tubes connected to it for supplying a fluid to the chamber and removing fluid from the chamber. These tubes can become tangled or snagged as the chambers are moved. Having to move a large number of chambers with their associated tubing would be much more complicated than moving one or a few actuators. Moving the chambers might also be detrimental to the samples contained in the chambers or affect their properties in a non-desirable and/or unknown way. Moving the chambers results in the biologic samples being subject to mechanical stimulation due to the movement that depending on the frequency and magnitude could negatively affect biologic sample properties and/or become an unknown stimulation parameter. Fixed actuators with movable chambers are less flexible for adapting the cadence and type of loading. For example, with turret style chamber movement, the cadence and sequence of sample stimulation is more rigidly constrained. Alternatively, the chambers could be fixed with a dedicated actuator or actuators for each sample chamber. Such an arrangement, however, would be inefficient and expensive.

Figure 1:
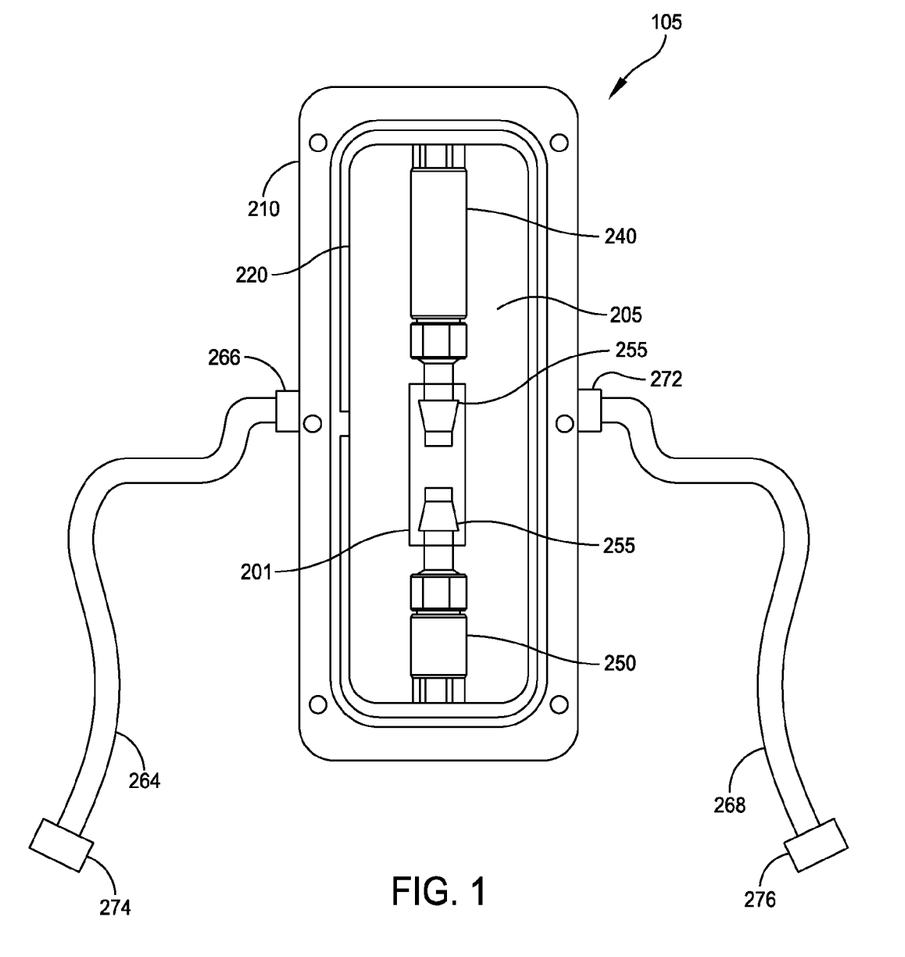
FIG. 1 is a front view of a portion of a biologic sample chamber.

FIG. 1 illustrates a front view of a portion of a biologic sample chamber 105. Typically, the biologic sample chamber is manually prepared in a clean environment by an operator using a dedicated set-up fixture (not shown). The biologic sample chamber 105 includes a chamber housing 210 that encloses a chamber volume 205. The chamber housing 210 may include a transparent or translucent chamber window 220 allowing automated visual monitoring and measurement of a biologic sample 201. The biologic sample chamber may be configured to accommodate a variety of biologic sample grips (i.e. biologic sample holders) according to the type of biologic sample. Grips can be custom-made for a particular type of biologic sample. For example, pincher-type grips may be used to hold a strip such as a ligament, tendon, or skin biologic sample. Porous or non-porous platens may be used to hold disk-shaped biologic samples such as cartilage or bone. Three- or four-point bend fixtures may be used to condition biologic samples in the chamber such as bone. In the configuration shown in FIG. 1, an upper biologic sample grip 240 and a lower biologic sample grip 250 are configured to hold a tubular biologic sample 201 such as a vessel with or without a valve, urethra, bladder or trachea. The tubular biologic sample grips each have an end fitting 255 such as, for example, a nozzle or barb fitting that holds an end of the tubular biologic sample.

Figure 2:
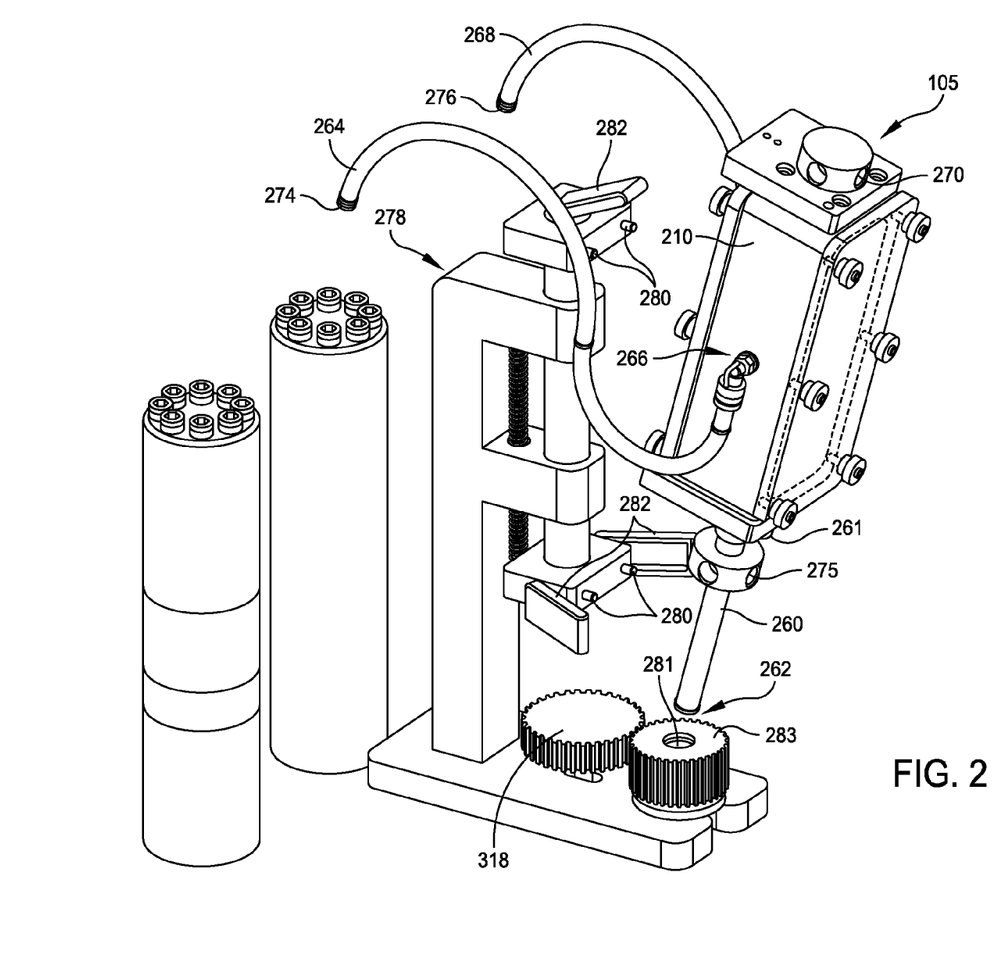
FIG. 2 is a schematic perspective view of the biologic sample chamber of FIG. 1 being loaded into a support structure.

Referring to FIGS. 1 and. 2, the lower biologic sample grip 250 is mechanically coupled to a shaft 260 that extends from the chamber housing 210 such that a free end of the shaft 260 is external to the chamber 105. The shaft 260 is connected to a feature 262 that engages with an actuator (described below) that is used to apply a load in one or more axes (e.g. stress, strain, bend) to a biologic sample in the chamber. The lower biologic sample grip 250 and chamber housing (210) are connected by a flexible fluid seal that allows for unconstrained motion of the shaft relative to the fixed chamber. As such, the grip 250 mechanically transmits a user-defined conditioning profile (i.e. load) generated by the actuator to the held biologic sample. The upper biologic sample grip 240 may be set to a fixed position by the operator relative to the chamber housing 210, or in some cases may also utilize a seal to transmit motion or force to actuator(s) or sensor(s).

When initially setting up the chamber 105, a operator removes the window 220 to secure the biologic sample 201 to the biologic sample grips 240, 250. The operator then manually turns a thumb screw 261 (see also FIG. 6) to lock the lower biologic sample grip in place. A non-damaging thumb screw is preferably used (e.g. brass dog point, soft flat point, etc). Alternatively, a manually activated shaft clamp collar could be used. The window 220 is then secured to the chamber 105 to hermetically seal the chamber. A first end of a conduit 264 (e.g. tube) is connected to an opening in a left side of the chamber housing 210 by a quick connect fitting 266. Conduit 264 can be used to supply a fluid that may contain a nutrient to the external surfaces of the biologic sample in the chamber 105. A first end of a conduit 268 (e.g. tube) is connected to an opening in a right side of the chamber housing 210 by a quick connect fitting 272. Conduit 268 may be used to exhaust a fluid from the chamber 105. Quick connect fittings 274 and 276 are located at respective second ends of the conduits 264 and 268.

The operator then uses a pump (not shown) to fill up the conduits 264 and 268 with fluid as well as to provide fluid to the chamber 105. In this example the chamber 105 will only be about half filled with fluid due to the locations of the fittings 266 and 272. Alternatively, another pair of fittings (not shown) located at or near a top of the chamber can be used if it is desired to have the chamber 105 completely filled with fluid. The biologic sample grips 240, 250 may be hollow to allow additional nutrient flow through the grips and biologic sample during the conditioning protocol. This is enabled by chamber ports 270, 275 which provide fluid communication between the grips 240, 250, the biologic sample 201, and an external nutrient fluid circuit (not shown). The details of the nutrient fluid management system and control along with the instrumentation and system controls that may be used is described in U.S. Pat. No. 7,587,949, herein incorporated by reference in its entirety.

With reference to FIG. 2, the chamber 105 with the conduits 264 and 268 is then carried by the operator to a support structure 278 which can removably hold the biologic sample chamber 105. The structure 278 may be contained within an incubator which can hold a large number of chambers and provide a controlled environment (e.g. temperature, humidity, gas environment) to the biologic samples. The operator aligns four mounting features (e.g. blind holes (not shown)) on the back of the chamber 105 with four alignment pins 280 on the support structure 278 and presses the chamber 105 onto the support structure 278. The shaft 260 is inserted through a bore 281 in a radial clamping device such as a lock/unlock gear 283 that is part of the support structure 278. A set of latches 282 is used to secure the chamber 105 to the structure 278.

Figure 3:
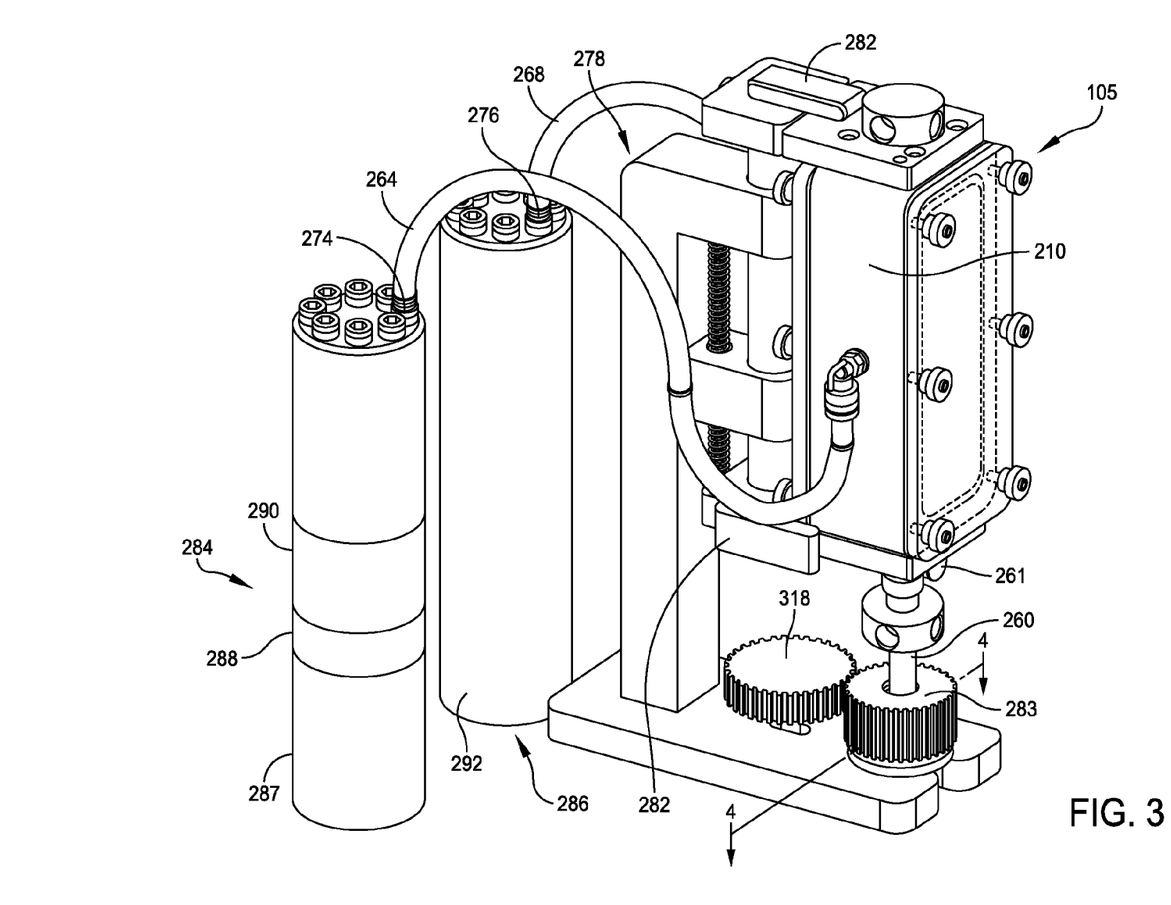
FIG. 3 is a schematic perspective view of the biologic sample chamber of FIG. 1 after it is loaded into the support structure.

FIG. 3 shows the chamber 105 mounted to the support structure 278 with the latches 282 in a closed position. The operator then connects fittings 274 and 276 (and thus the ends of the conduits 264 and 268) to respective common conduit structures 284 and 286. Fluid is supplied to the chamber 105 from the structure 284. The structure 284 includes a fluid supply container 287, a filter 288, and a pump 290 (e.g. a peristaltic or gear pump). In this example, an additional seven conduits can be connected to the structure 284. This arrangement allows up to eight biologic sample chambers to be supplied with fluid from a single supply container 287, filter 288 and pump 290. In addition, the common conduit structures 284 and 286 help to keep the conduits 264, 268 etc. organized when a large number of biologic sample chambers are being used at the same time.

Likewise, fluid is transferred from the chamber 105 through the conduit 268 into the structure 286. Fluid from up to an additional seven chambers can be transferred into the structure 286. The structure 286 is mostly made up of a fluid container 292. In an alternative arrangement in which the fluid transferred from the chamber 105 (and other chambers) is to be recycled, the structure 286 is eliminated and the fitting 276 is connected to the container 287. This results in a closed loop fluid circulation system. The dynamic pressure and/or flow of the fluid can be controlled to apply additional loads continuously or periodically on the biologic sample 201 in the chamber 105.

Figure 4:
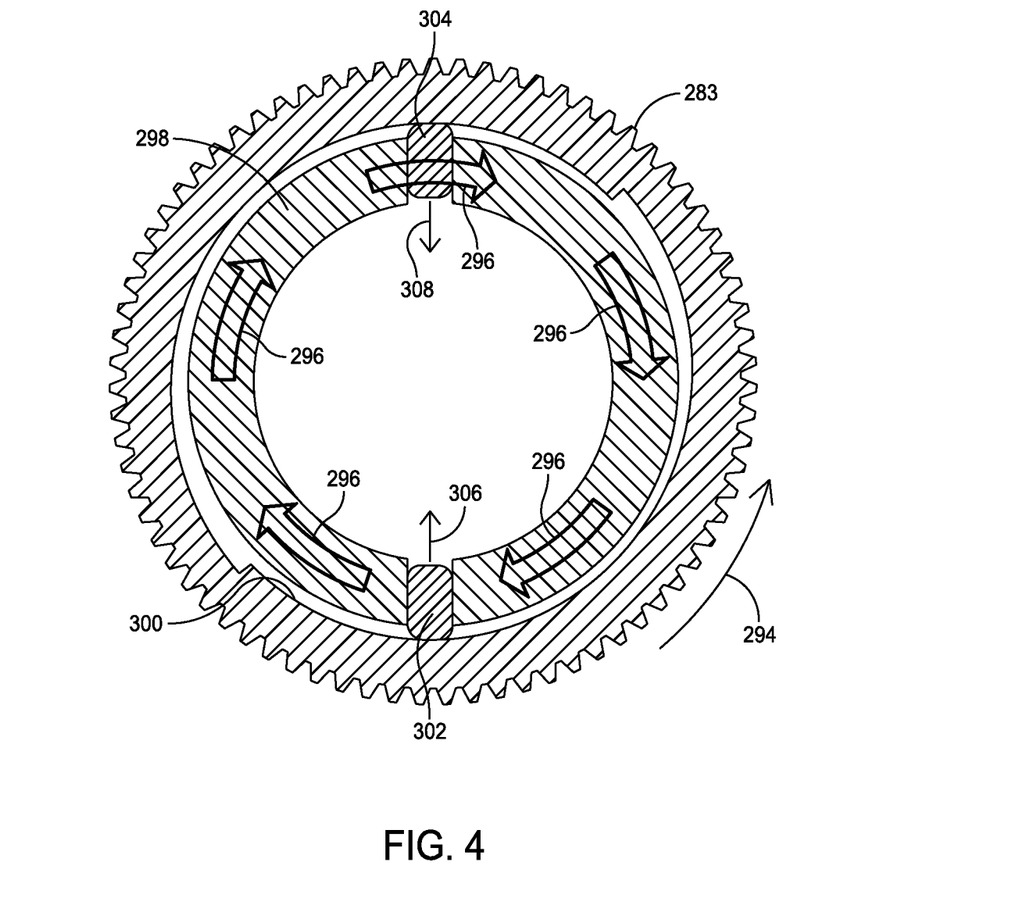
FIG. 4 is a partial sectional view of a lock/unlock mechanism (taken along the lines 4-4 of FIG. 3) that is shown in FIGS. 2 and 3.

Referring to FIGS. 3 and 4, the operator next manually rotates the gear 283 in the direction of an arrow 294 (counterclockwise). This rotation causes relative motion (represented by arrows 296) between the gear 283 and a stationary hub 298 which is fixed to the structure 278. The relative motion causes a cam surface 300 to push a pair of griping elements 302 and 304 in the respective directions shown by arrows 306 and 308. The elements 302 and 304 are thereby forced into pressurized contact with the shaft 260 of the chamber 105, thus holding the shaft 260 in a fixed position. As a last step, the operator rotates the thumb screw 261 (see FIG. 6) to release the shaft 260 from the grip of the thumb screw 261. The previous steps can be repeated for as many biologic samples and biologic sample chambers as are desired in the stimulation regime. As mentioned above, a large number of chambers can be placed into an incubator in which one or more actuators will stimulate the biologic samples. Once the biologic sample chambers are placed into the incubator, the incubator is closed up and the biologic sample stimulation regimen is commenced. More biologic samples can be added to or removed from the structure during the stimulation regime without affecting the existing or remaining biologic samples.

Figure 5:
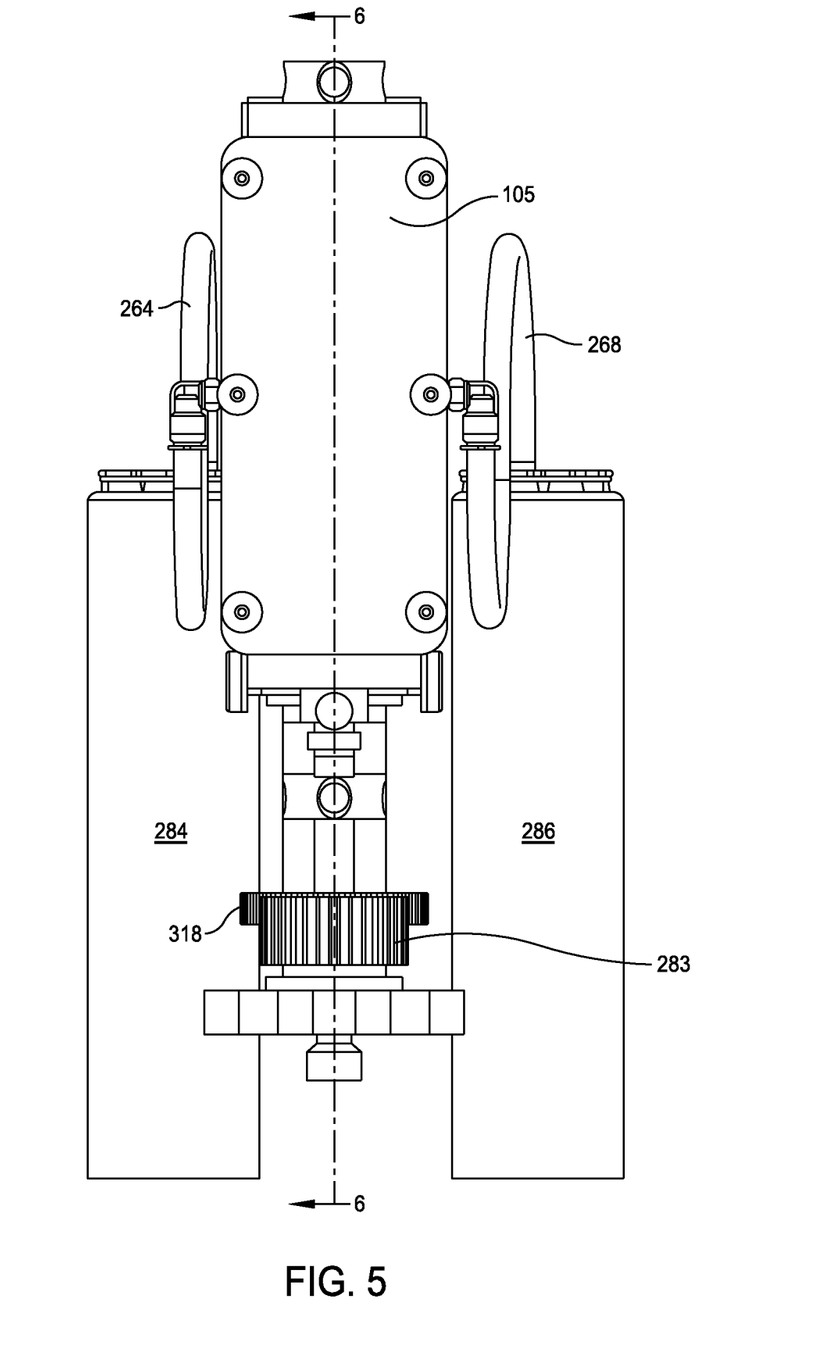
FIG. 5 is a front view of the apparatus shown in FIG. 3.
Figure 6:
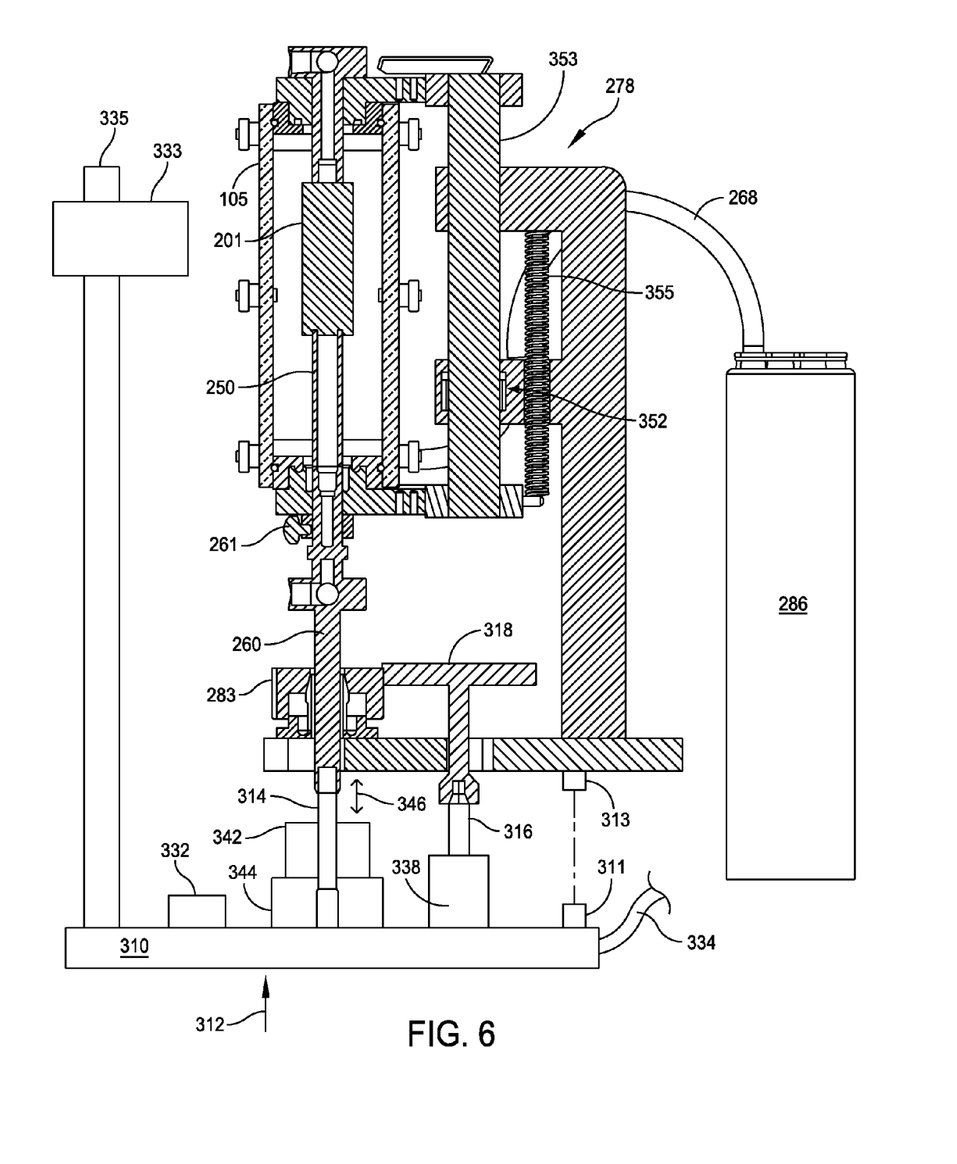
FIG. 6 is a sectional view taken along the lines 6-6 of FIG. 5.

Turning to FIGS. 5 and 6 and the biologic sample-engagement steps, the system now automatically positions an actuator stage 310 underneath the structure 278 using a machine positioning device 311 (e.g. a multiple axes machine vision system) which aligns on a feature 313 on the bottom of the support structure 278. The stage 310 is then automatically moved in a direction 312 to cause a driveshaft 314 to engage into the bottom of the shaft 260. This movement also causes a driveshaft 316 to be engaged into the bottom of a radial driving device such as a drive gear 318. As a result, stimulation actuators 342 and 344 (described further below) are automatically moved into a position proximate to the chamber 105 in which these actuators can transmit a load to the biologic sample 201 via a transmission path that includes the shaft 260 and the biologic sample holder 250.

Figure 7:
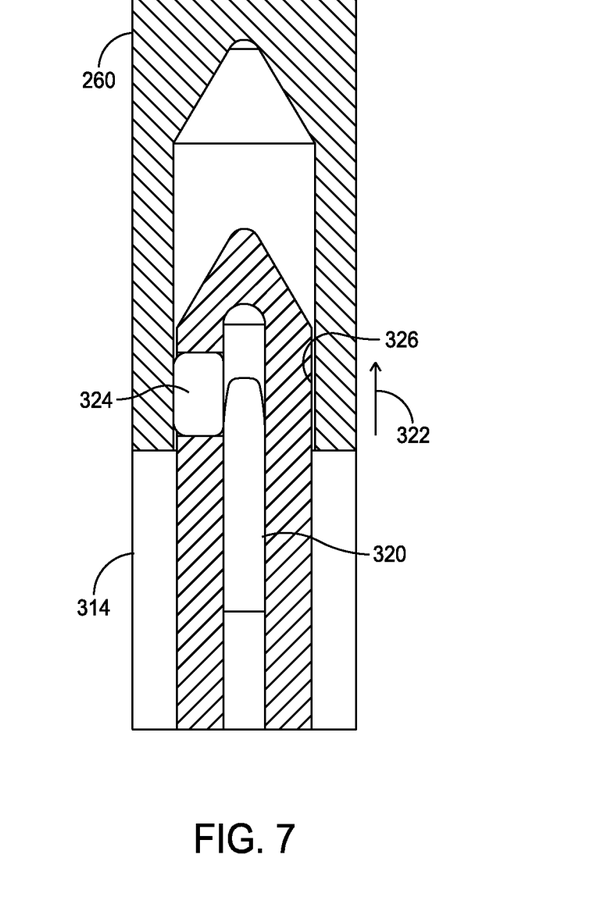
FIG. 7 is a partial sectional view of the interface between a driveshaft and a driven shaft.

With reference to FIG. 7, the interface between the driveshaft 314 and the shaft 260 will be described. After the driveshaft 314 has been inserted into the shaft 260, an internal pin 320 is moved in the direction 322, for example, by an electric solenoid. This movement causes the pin 320 to press against a lock component 324. There are multiple radially spaced components 324, but only one is shown in FIG. 7. The pressure from the pin 320 against the components 324 presses the components 324 into rigid compression with an internal surface 326 of the shaft 260 to create a rigid joint. The frictional resistance supplied by the components 324 against the surface 326 temporarily locks the drive shaft 314 to the shaft 260. As such, the driveshaft 314 can transfer load, displacement, torque and/or rotation to the shaft 260 with high rigidity. This same arrangement is used to temporarily lock the driveshaft 316 to the bottom of the drive gear 318 (see FIG. 6).

Referring to FIG. 6, a microcontroller 332 controls operation of all of the actuators (described below) and measurement of sensors in the motor assemblies on the stage 310. Cabling 334 supplies electrical power to the actuator stage 310 and control signals from a main controller (not shown) to the microcontroller 332. After the stage is moved into the position shown in FIG. 6 and the drive-shafts 314 and 316 are secured respectively to shaft 260 and gear 318, the microcontroller 332 causes the rotary engagement actuator 338 to operate to turn driveshaft 316 which turns drive gear 318. Gear 283 is turned in a clockwise direction (as viewed in FIG. 4) which releases the pressure on grips 302/304 and unlocks the shaft 260 from the grips 302/304. Movement of the shaft 260 is now controlled by the drive shaft 314 and the stimulation actuators 342 and 344.

One or more measurement devices can be used to obtain characteristics of the sample. These devices can travel with the actuator stage (or a separate measurement stage) and/or remain with the sample or chamber even when the actuator stage is moved away from the chamber. The load on the sample can be measured by monitoring electrical current in motor 342 or by a load cell in the force transmission path to the sample. A measurement device 333 (e.g. a laser micrometer or CCD camera) is supported on a member 335 that extends from the stage 310. The device 333 is used to measure a characteristic (e.g. dimension) of the biologic sample 201 at any time while the stage 310 is in the position shown in FIG. 6. Other types of sensors include those to measure, for example, temperature, torque, rotation, strain, electrical properties, magnetic field, and chemical composition.

The previous steps outline the engagement of the stimulation actuators 342 and 344 to the biologic sample 201. Now that the actuators 342 and 344 are engaged to the biologic sample, and the associated sensors are in place, the stimulation step can occur. The microcontroller 332 now operates the linear actuator 342 and/or the rotary actuator 344 to move the driveshaft 314 which in turn moves the shaft 260. The linear actuator 342 (e.g. a linear electromagnetic motor) can move the driveshaft 314 back and forth in the directions shown by two-headed arrow 346. This can be in various control modes depending on the desired stimulation profile (e.g. stress or strain control). The rotary actuator 344 (e.g. a rotary electro-magnetic motor) can rotate the linear actuator 342 in either torque (stress) or rotation (strain) control and thus the drive shaft 314 about an axis running down the center of the drive shaft 314. Movement of the shaft 260 causes the lower biologic sample grip 250 to likewise move. This movement in turn applies tension, compression and/or rotary stresses to the biologic sample 201. As such, the actuators 342 and 344 supply a load to the biologic sample 201 that is held by the biologic sample holders 240 and 250. The microcontroller 332 can vary the duration, frequency and amplitude of the linear and rotary motion imparted to the shaft 260 to control the mechanical stimulation that is applied to the biologic sample 201. At various stages of the development cycle, alternate stimulation actuators can be deployed and engaged. These various sequences can be manually pre-described by the operator or automatically adaptive based on biologic sample measurements acquired and analyzed during previous loading cycles.

The operator (user) can define a conditioning profile with fixed periods of conditioning and rest for one or more biologic samples. Alternatively, the operator can define a conditioning profile that depends on a variable. For example, a 1 HZ tension-compression load can be applied to the biologic sample until the sample elongates by a certain specified percentage (e.g. 20%) If the microcontroller 332 and/or the main controller (mentioned above) is going to base the conditioning on a variable (e.g. elongation), the chamber will need the appropriate sensor to measure the variable. A signal from such sensor will be fed back to the microcontroller 332 and/or the main controller via a wired and/or wireless transmission path. In some embodiments a user interface (not shown) for the microcontroller 332 and/or main controller may be collocated with the system or it may be remote from the rest of the system. For example, a web based user interface can be used that permits a researcher to program a conditioning profile from anywhere. The entire system with multiple biologic sample chambers may be located within an incubator, or there may be multiple incubators for different sets of chambers, or each chamber can be located within its own incubator. In another example, a fluid pump such as a bellows or diaphragm (not shown) is included in the chamber 105. An additional actuator (not shown) is included on the stage 310 and operates the fluid pump to pulse pressure waves through fluid inside the chamber 105, thereby providing further stimulation to the biologic sample 201.

Once the mechanical stimulation cycle for the biologic sample 201 has been completed (i.e. the microcontroller 332 has stopped the linear and rotary actuators 342 and 344), the following sequence occurs to disengage the actuator stage 310 from the support structure 278. First, the microcontroller operates one or both actuators 342 and 344 to place the biologic sample in an unloaded state (measured by a respective sensor in each of the actuators 342 and 344). Next, an electric shaft clamp 352, which to this point has locked a shaft 353 in place, is released by the microcontroller 332. The shaft 353 may now be moved up or down relative the support structure 278. A spring, or spring set, 355 is connected at a bottom end to a feature projecting from the shaft 353 and at a top end to the support structure 278. The spring 355 is in tension at this point and is arranged to maintain the shaft 353 and thus chamber 105 in the same position as it was before clamp 352 was released. Instead of or in addition to the spring 355, another force provider such as a pneumatic, hydraulic, magnetic or other system may be provided.

If it is desired to automatically maintain a constant load on the sample 201 after the stage 310 is moved away, the following steps may be taken. The microcontroller operates one or both actuators 342 and 344 to place the biologic sample in a loaded state (measured by a respective sensor in each of the actuators 342 and 344). For example, the shaft 314 can be moved downward to place the sample 201 in tension. The spring 355 provides force in an upward direction to bias the chamber 105 upwards. A relatively long spring 355 is used in order to keep a substantially constant force on the sample 201 even if the sample relaxes (e.g. elongates). If it is desired to automatically adjust the load on the sample 201 over time, the spring 355 is replaced by, for example, a pneumatic or hydraulic force provider. The steps described above in this paragraph are used only if the sample 201 is to be left in a load-controlled state (to prevent relaxation and loss of specimen load and stress_. These steps are skipped it is desired to leave the sample in a fixed displacement position.

The microcontroller 332 now operates the rotary actuator 338 to turn the gear 283 in a counter-clockwise direction (see FIG. 4) via the drive gear 318. This rotation drives the grips 302/304 in the respective directions of arrows 306/308, thereby impinging the grips 302/304 on the shaft 260. This has the effect of locking the shaft 260 in place.

With reference to FIGS. 6 and. 7, the pin 320 is now moved by a solenoid (not shown) in a direction opposite to that shown by the arrow 322. As such, the pin 320 is disengaged from the components 324. The frictional resistance of the components 324 against the surface 326 is thereby released which allows the driveshaft 314 to be withdrawn from the shaft 260. This same procedure is used at the interface of the driveshaft 316 from the gear 318. Now the actuator stage 310 is lowered in a direction opposite to the arrow 312 to disengage the drive shafts 314 and 316 respectively from the shaft 260 and the gear 318. The stage 310 can now be moved to another chamber/support structure to provide mechanical stimulation to a biologic sample in that chamber.

Turning to FIG. 8, an example is provided in which a two-dimensional array of biologic sample chambers 105A, 105B etc. are shown arranged in two rows. Some features of the previous figures have been removed from FIG. 8 in order to avoid over-cluttering FIG. 8. The actuator stage 310 is supported by a first screw-drive system 360 which can be operated to move the stage 310 in the directions shown by two-headed arrow 362. The system 362 is supported by a platform 364 of a second screw-drive system 366 which can be operated to move the platform 364 in the directions shown by a two-headed arrow 368. A solenoid or other type of drive system (not shown) is located between the system 360 and the platform 364, and is used to move the system 360 in the directions shown by a two-headed arrow 370. As such, the actuator stage 310 can be moved in three dimensions to connect and disconnect the drive shafts 314 and 316 (FIG. 6) from the various chambers.

For example, the stage 310 can be automatically lowered from a first position in which it is engaged with the chamber 105A to a second position in which the actuators 342 and 344 cannot transmit a load to a biologic sample in chamber 105A. The stage 310 can then be automatically moved to a third position proximate to a second biologic sample chamber 105B having a second biologic sample holder therein so that the actuators 342 and 344 can transmit a load to a biologic sample held by the second biologic sample holder via a transmission path that includes the shaft 260 and the second biologic sample holder.

Figure 9:
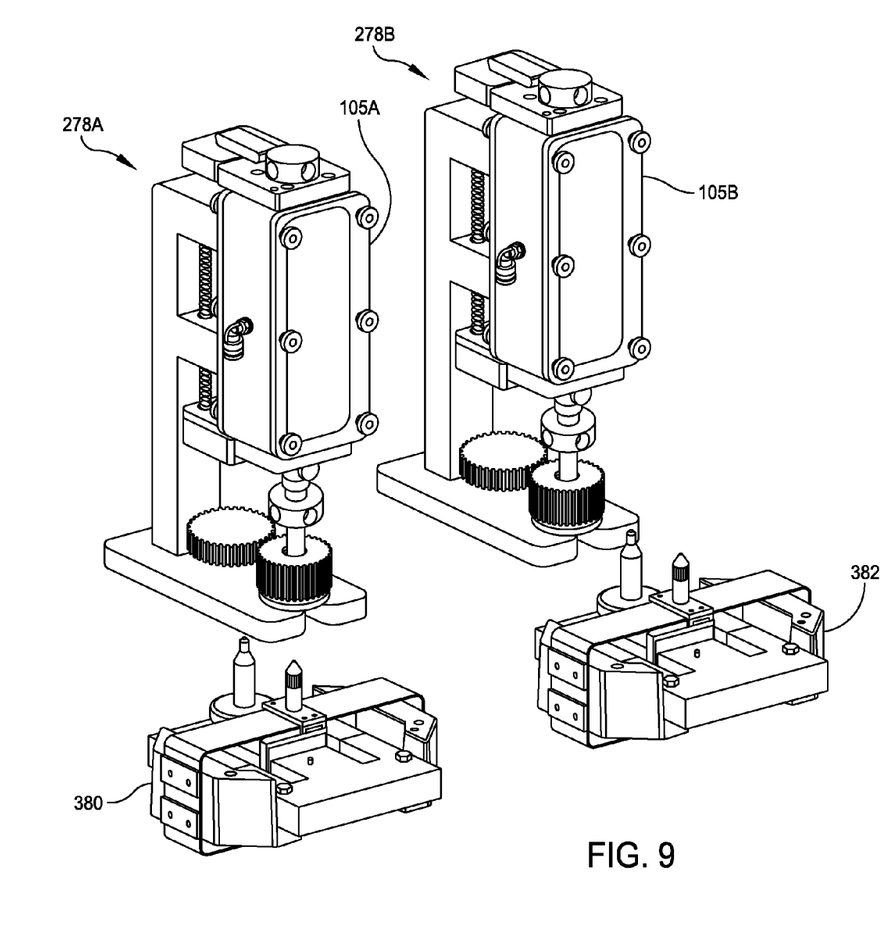
FIG. 9 is a perspective view of an example with two biologic sample chambers and two actuator stages.

Referring to FIG. 9, an example is shown in which two stages 380 and 382 are provided. Two support structures 278A and 278B are also shown along with two biologic sample chambers 105A and 105B. Each of the stages 380 and 382 is generally similar to the stage 310 described above. Stages 380 and 382 can be essentially identical, or these two stages can be substantially different from each other. One difference the stages 380 and 382 can have with each other is to have substantially different actuators for supplying a load to a biologic sample in a biologic sample chamber. For example, stage 380 may have a lower power/stroke actuator for providing a smaller load to a biologic sample during an earlier stage of biologic sample loading. In a later stage of biologic sample loading, stage 382 can be automatically moved into the position previously occupied by stage 380 in order to supply a larger load to the same biologic sample with a higher power/stroke actuator. Structure for moving the stages 380 and 382 is not shown in FIG. 9, but structure similar to that shown in FIG. 8 can be used to move each of these stages from engagement with chamber 105A to engagement chamber 105B to a neutral position not engaged with either chamber.

Referring to FIG. 6, another example will be described. A second set of gears (not shown) similar to gears 283 and 318 is arranged above the chamber 105 and supported by the support structure 278. An additional shaft (not shown) similar to shaft 260 extends from the top of the chamber 260. The stage 310 can be moved so that shafts 314 and 316 engage the additional shaft and one of the second set of gears respectively. Now the actuators 342 and 344 can stimulate the sample 201 from above the chamber. Alternatively, an additional stage that may be the same as or different from the stage 310 is moved above the chamber 105. This can be done either when stage 110 is positioned under the chamber 105 or when the stage 110 is remote from the chamber 105. As such, the sample 201 can receive stimulation from both sample grips 240 and 250. If the additional stage has one or more actuators that are different from the actuators on the stage 310, then a different type of stimulation can be provided to the sample 201 by the actuator(s) of the additional stage compared to the actuators 342 and 344 of the stage 310.

Having thus described at least illustrative embodiments, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed:

1. A system for applying mechanical stimulation to a biologic sample, the system comprising:
a first biologic sample chamber having a biologic sample holder therein;
a support structure for holding the first biologic sample chamber;
a first actuator that can supply a mechanical load to a biologic sample held by the biologic sample holder, the actuator configured to move into a first position proximate to the chamber in which the actuator can transmit the load to the biologic sample via a first transmission path that includes the biologic sample holder;
a controller configured to automatically move the first actuator into the first position; and
a second actuator which is substantially different from the first actuator, the second actuator being automatically movable into the first position when the first actuator is not in the first position so that the second actuator can transmit a load to the first biologic sample holder via the first transmission path.

2. The system of claim 1, wherein the first actuator can be automatically moved to a second position in which the first actuator cannot transmit the load to the biologic sample.

3. The system of claim 1, wherein the first actuator can be automatically moved to a third position proximate to a second biologic sample chamber having a second biologic sample holder therein so that the first actuator can transmit a load to a biologic sample held by the second biologic sample holder via a transmission path that includes the second biologic sample holder.

4. The system of claim 1, wherein the second actuator can be automatically moved to a second position in which the second actuator cannot transmit a load to the first biologic sample, wherein the second actuator can be automatically moved to a third position proximate to a second biologic sample chamber having a second biologic sample holder therein so that the second actuator can transmit a load to a biologic sample held by the second biologic sample holder via a transmission path that includes the second biologic sample holder when the first actuator is not in the third position.

5. The system of claim 4, wherein each biologic sample chamber includes a first opening through which a fluid can be supplied to a biologic sample in that chamber, and wherein a first end of respective supply conduits is connected to each opening for conducting fluid to that opening, a second end of each respective conduit is connected to a first common conduit structure and wherein each biologic sample chamber includes a second opening through which a fluid can be transferred from that chamber, and wherein a first end of respective exhaust conduits is connected to each second opening for conducting fluid from the second opening, a second end of each respective conduit is connected to a second common conduit structure.

6. The system of claim 1, wherein the biologic sample is a living tissue sample.

7. The system of claim 1, wherein the actuator is an electromagnetic actuator.

8. The system of claim 1, wherein the controller causes the actuator to deliver the load.

9. The system of claim 8, wherein the controller is programmable by a user.

10. The system of claim 9, wherein the controller is configured to deliver the load for a user-defined period of time.

11. The system of claim 9, wherein the controller is configured to deliver the load according to a user-defined conditioning profile.

12. The system of claim 11, wherein the user-defined conditioning profile delivers the load to the biologic sample based upon one or more fixed-time profiles.

13. The system of claim 11, wherein the user-defined conditioning profile delivers the load to the biologic sample based upon a value of a measured variable.

14. The system of claim 13, wherein the measured variable consists of one or more of the following: temperature in the chamber, pH in the chamber, and a property of the biologic sample.

15. The system of claim 2, wherein after the actuator is moved away from the first position, a load on the biologic sample can be automatically maintained.

16. The system of claim 4, further including a fluid pump that can be operated to transmit pressure through a fluid in the chamber to thereby stimulate the biologic sample.

17. A system for applying mechanical stimulation to a biologic sample, the system comprising:
   a first biologic sample chamber having a biologic sample holder therein;
   a support structure for holding the first biologic sample chamber;
   a first actuator that can supply a first load to a biologic sample held by the biologic sample holder, the actuator being automatically movable into a first position proximate to the chamber in which the actuator can transmit the first load to the biologic sample via a first transmission path that includes the biologic sample holder; and
   a second actuator which can supply a second load to the biologic sample, the second actuator being automatically movable into the first position when the first actuator is not in the first position so that the second actuator can transmit the second load to the biologic sample via the first transmission path.

18. The system of claim 17 in which the second actuator is substantially different from the first actuator.

19. The system of claim 17, wherein the first actuator can be automatically moved to a second position in which the actuator cannot transmit a load to the biologic sample.

20. The system of claim 19, further including a second biologic sample chamber having a biologic sample holder therein, the support structure being capable of removably holding the second biologic sample chamber, the first actuator being automatically movable into a third position in which the first actuator is proximate to the second chamber so that the first actuator can transmit the first load to a biologic sample in the second chamber via a second transmission path that includes the second chamber's biologic sample holder.

21. The system of claim 20, wherein the second actuator can be automatically moved into the third position when the first actuator is not in the third position so that the second actuator can transmit the second load to a biologic sample in the second chamber via the second transmission path.

22. The system of claim 20, wherein each biologic sample chamber includes an opening through which a fluid can be supplied to a biologic sample in that chamber, and wherein a first end of respective conduits is connected to each opening for conducting fluid to that opening, a second end of each respective conduit is connected to a common conduit structure.

23. The system of claim 20, wherein each biologic sample chamber includes an opening through which a fluid can be transferred from that chamber, and wherein a first end of respective conduits is connected to each opening for conducting fluid from the opening, a second end of each respective conduit is connected to a common conduit structure.

24. The system of claim 17, wherein the biologic sample is a living tissue sample.

25. The system of claim 17, wherein the first and second actuators are each an electromagnetic actuator.

26. The system of claim 17, wherein after the first actuator is moved away from the first position, a load on the biologic sample can be automatically maintained.

27. A method for applying mechanical stimulation to a biologic sample, comprising the steps of:
   providing a first biologic sample chamber having a biologic sample holder therein for holding a biologic sample, the chamber having a first opening through which a fluid can be supplied to the biologic sample and a second opening through which a fluid can be transferred from the chamber, the first and second openings having connected thereto a first end of respective conduits extending therefrom for conducting fluid;
   attaching the chamber to a support structure which can removably hold the biologic sample chamber;
   automatically moving a first actuator that can supply a load to the biologic sample into a first position in which the actuator is proximate to the chamber whereby the actuator can transmit a load to the biologic sample by a first transmission path that includes the biologic sample holder; and
   providing a second actuator which is substantially different from the first actuator, the second actuator being automatically movable into the first position when the first actuator is not in the first position so that the second actuator can transmit a load to the biologic sample in the first chamber via the first transmission path.

28. The system of claim 27, wherein the first actuator can be automatically moved to a second position in which the first actuator cannot transmit a load to the biologic sample.

29. The method of claim 28, further including the step of automatically moving the first actuator to a third position in which the first actuator is proximate to a second chamber such that the first actuator can transmit a load to a biologic sample in the second chamber via a second transmission path that includes a biologic sample holder in the second chamber.

30. The method of claim 29, wherein the second actuator is automatically movable into the third position when the first actuator is not in the third position so that the second actuator can transmit a load to a biologic sample in the second chamber via a second transmission path that includes a biologic sample holder in the second chamber.

31. The method of claim 27, wherein the biologic samples are living tissue samples.

32. The method of claim 27, wherein the first actuator is an electromagnetic actuator.

33. The method of claim 28, wherein after the first actuator is moved to the second position, a load on the biologic sample can be automatically maintained.

34. The method of claim 27, wherein the first actuator includes a driveshaft, wherein a shaft extends from the biologic sample holder such that a free end of the shaft is external to the chamber, the shaft forming part of the first transmission path, wherein moving the first actuator into the first position causes the driveshaft to be engaged with the shaft such that the driveshaft and shaft can be temporarily locked together.

35. A system for applying mechanical stimulation to a biologic sample, the system comprising:
   a first biologic sample chamber having a biologic sample holder therein;
   a support structure for holding the first biologic sample chamber;
   a first actuator that can supply a mechanical load to a biologic sample held by the biologic sample holder, the actuator configured to move into a first position proximate to the chamber in which the actuator can transmit the load to the biologic sample via a first transmission path that includes the biologic sample holder;
   a second actuator which is substantially different from the first actuator, the second actuator being automatically movable into the first position when the first actuator is not in the first position so that the second actuator can transmit a load to the biologic sample in the first chamber via the first transmission path;

a measurement device for obtaining one or more characteristics of the biologic sample; and a controller configured to automatically move the first and second actuators into the first position.

36. The system of claim 35, wherein the measurement device moves with the first actuator.

37. The system of claim 35, wherein the measurement device remains with the chamber even when the first actuator is moved away from the chamber.

* * * * *